US00PP25019P2

(12) United States Plant Patent
Egger

(10) Patent No.: US PP25,019 P2
(45) Date of Patent: Oct. 28, 2014

(54) ***HEUCHERA* PLANT NAMED 'GLITTER'**

(50) Latin Name: ***Heuchera* hybrid**
Varietal Denomination: Glitter

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 39 days.

(21) Appl. No.: 13/986,392

(22) Filed: Apr. 26, 2013

(51) Int. Cl.
*A01H 5/00* (2006.01)

(52) U.S. Cl.
USPC ..... Plt./440

(58) Field of Classification Search
CPC ..... A01H 5/02
USPC ..... Plt./440
See application file for complete search history.

*Primary Examiner* — June Hwu
*Assistant Examiner* — Keith Robinson
(74) *Attorney, Agent, or Firm* — Klarquist Sparkman, LLP

(57) ABSTRACT

A new and distinct *Heuchera* plant characterized by medium size silver leaves with prominent dark veins, hot pink flowers on dark, well branched inflorescences, a medium, mounding habit, and excellent vigor.

1 Drawing Sheet

Botanical denomination: *Heuchera* hybrid.
Variety designation: 'Glitter'.

BACKGROUND

The present invention relates to a new and distinct cultivar of *Heuchera* and given the cultivar name of 'Glitter'. *Heuchera* is in the family Saxifragaceae. *Heuchera* 'Glitter' originated from an open pollinated cross of *Heuchera* 'Tango', U.S. Plant Pat. No. 17,133, in the trial beds in Canby, Oreg. The new cultivar was chosen for its vigor, silver leaves, and showy flowers.

Compared to the seed parent, *Heuchera* 'Tango', U.S. Plant Pat. No. 17,133, the new cultivar is a larger more vigorous plant, with leaves that are larger and much more silver, and it is less free flowering. The tendency to be so free flowering made *Heuchera* 'Tango' hard to produce as it bloomed at a very small size and never stopped.

Compared to *Heuchera* 'Silver Scrolls', U.S. Plant Pat. No. 12,066, the new cultivar has shorter inflorescences with hot pink rather than white flowers.

Compared to *Heuchera* 'Sugar Plum', U.S. Plant Pat. No. 21,859, the new cultivar has more crowns, smaller leaves, leaves that have less purple coloration, and darker pink flowers.

This new *Heuchera* is uniquely distinguished by:

1. medium size silver leaves with prominent dark veins,
2. hot pink flowers on dark, well branched inflorescences,
3. a medium, mounding habit,
4. and excellent vigor.

This new cultivar has been reproduced only by asexual propagation (tip cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWING

FIG. 1 shows a 9 month-old plant of *Heuchera* 'Glitter' growing in a 1 gallon pot in a cool greenhouse in early July in Canby, Oreg.

DETAILED PLANT DESCRIPTION

The following is a detailed description of the new *Heuchera* cultivar based on observations of 1-year-old specimens growing in full sun in the trial bed in October in Canby, Oreg. Canby is Zone 8 on the USDA Hardiness map. Temperatures range from a high of 95° F. in August to and average of 32° F. in January. Normal rainfall in Canby is 42.8 inches per year. The color descriptions are all based on The Royal Horticultural Society Colour Chart, $5^{th}$ edition, 2007.

Plant:

*Form.*—Basal rosette, herbaceous perennial.
*Hardiness.*—USDA Zone 4 to 9.
*Size.*—18 cm tall from top of the foliage to the soil and 38 cm wide.
*Habit.*—Mounding.
*Vigor.*—Excellent.

Leaf:

*Type.*—Simple.
*Arrangement.*—Rosette.
*Number.*—About 100.
*Shape.*—Broadly ovate to orbicular.
*Lobing/division.*—5 to 7 shallow lobes.
*Venation.*—Palmate.
*Margins.*—Crenate.
*Apex.*—Mucronulate.
*Base.*—Cordate, usually overlapping.
*Blade size.*—Grows to 10 cm long and 9.8 cm wide.
*Texture.*—Supple, somewhat glossy, not rugose.

*Surface texture*.—Glandular on both sides.

*Petiole description*.—Grows to 12 cm long and 3 mm wide, glandular hairs, closest to Brown 200C.

*Leaf color*.—Topside, spring to summer leaves closest to Black 202D with veins Greyed Purple N187A, bottom side closest to Purple N77A; fall to winter leaves topside closest to Black 202D tinted Greyed Purple N187A with veins Greyed Purple N187A, bottom side closest to Purple N77A.

Inflorescence:

*Size*.—Grows to 19 cm wide and 39 cm long.

*Type*.—Thyrse to branched thyrse.

*Number of flowers per peduncle*.—60 to 1000 depending on the number of branches.

*Number of thyrse*.—0 to 9.

*Peduncle*.—Grows to 45 cm long, 9 mm wide at base, Purple N77A, glandular hairs.

*Pedicel*.—Variable in size, with glandular hairs, Purple N77A.

*Bloom period*.—July to October in Canby, Oreg.

Flower bud:

*Size*.—3.5 mm wide and 6 mm long.

*Description*.—Glandular puberulent, ovoid, down facing.

*Color*.—Red Purple 59C on the bottom ⅓ and 63B on the top ⅔.

Flower:

*Type*.—Perfect.

*Shape*.—Campanulate.

*Size*.—9 mm long and 4 mm wide.

*Corolla description*.—5 petals, 4 mm long and 1.5 mm wide, broadly spatulate, margins entire, tip acute, glabrous top and glandular on bottom, both sides Red Purple 62A on top ½ and 62D on bottom ½.

*Calyx description*.—Campanulate, 9 mm long and 4 mm wide, with 5 lobes divided ⅔ way to the base, each 2.5 mm wide and 3 mm long, glandular hairs both sides, tips acute, margin entire; color outside and inside Red Purple 63A on tip blending to 63B on lobes, 63C below in a band on the outside below the lobes (staying 63C inside below the lobes) then darkening to 59C on bottom outside.

*Stamen description*.—5 in number, 3.2 mm long, filaments 3 mm long, White NN155C, anthers 0.2 mm, Orange 25A, pollen none.

*Pistil description*.—1, 2-beaked, 6 mm long and 2 mm wide, White NN155C overall; ovary 2 mm long and 2 mm wide, style 4 mm long.

*Fragrance*.—None.

*Lastingness*.—Each thyrse blooms for about 4 weeks on the plant.

Fruit:

*Type*.—Two-beaked ovoid capsule.

*Size*.—8 mm long and 3 mm.

*Fertility*.—Low.

*Color*.—Greyed Brown 199C.

Seed:

*Shape*.—Linear.

*Size*.—2 mm long.

*Color*.—Black 202A.

Pest and disease tolerance: The new cultivar is typical to the genus. No known resistances to pests or diseases. No problems have been found in Canby, Oreg.

I claim:

1. A new and distinct *Heuchera* plant as herein illustrated and described.

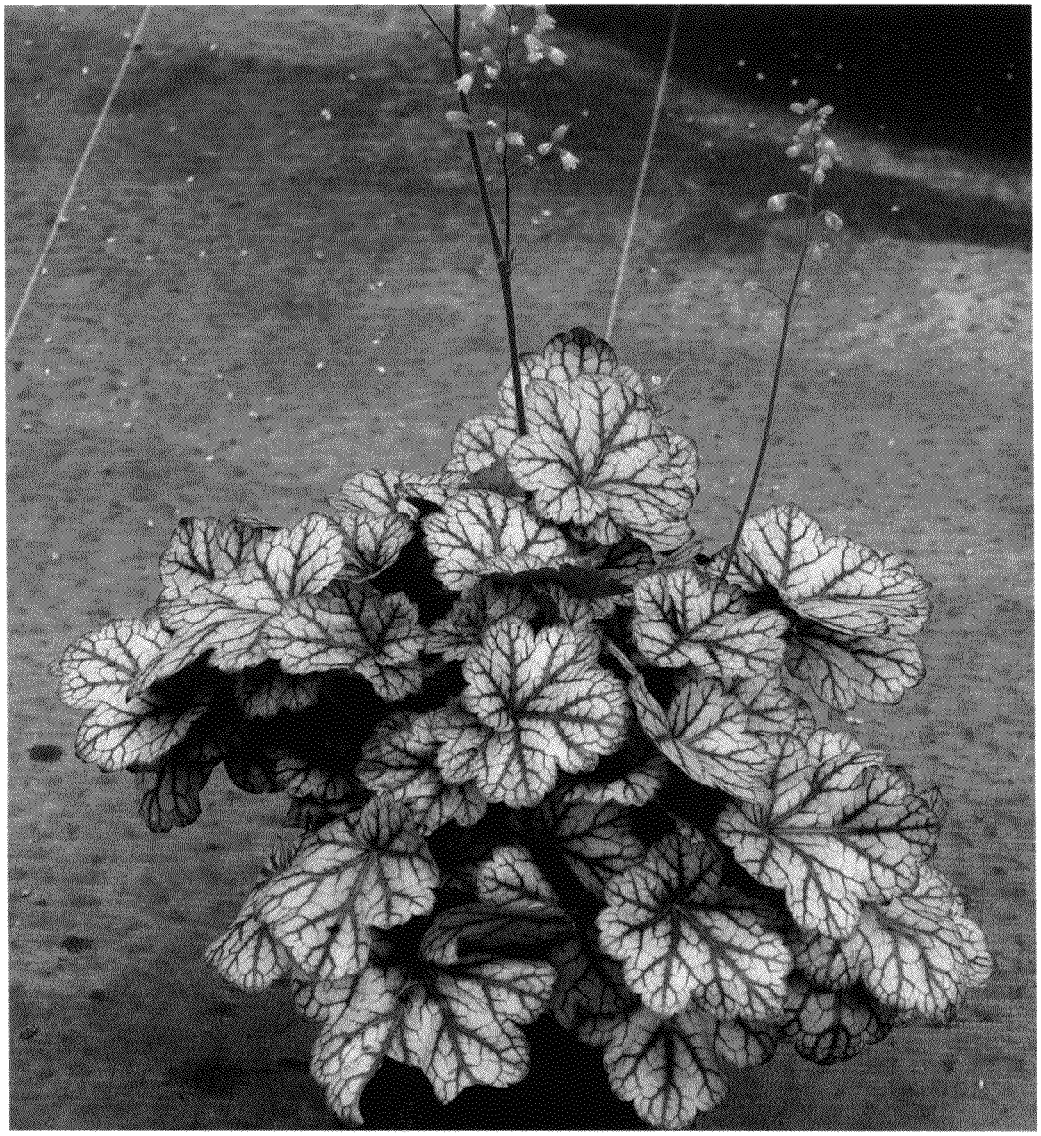

* * * * *